United States Patent [19]
Yamanishi et al.

[11] Patent Number: 5,385,144
[45] Date of Patent: Jan. 31, 1995

[54] RESPIRATION DIAGNOSIS APPARATUS

[75] Inventors: Akio Yamanishi, Hyogo; Kenji Hamaguri, Osaka, both of Japan

[73] Assignee: Minolta Co., Ltd., Osaka, Japan

[21] Appl. No.: 95,296

[22] Filed: Jul. 21, 1993

[30] Foreign Application Priority Data

Jul. 23, 1992 [JP] Japan .................................. 4-197085

[51] Int. Cl.⁶ .............................................. A61B 5/08
[52] U.S. Cl. ..................................... 128/633; 128/666; 128/716; 128/671
[58] Field of Search .................. 128/633-634, 128/664-665, 666, 670-671, 716, 721-724; 607/62

[56] References Cited
U.S. PATENT DOCUMENTS 4,777,962  10/1988  Watson et al. ................... 128/721 X
4,802,485   2/1989  Bowers et al. ...................... 128/633
5,146,916   9/1992  Kallok et al. ..................... 607/62 X

OTHER PUBLICATIONS

The Japanese Journal of Thoracic Diseases, Special Edition, (vol. 30), Apr. 1992.

*Primary Examiner*—Angela D. Sykes
*Attorney, Agent, or Firm*—Price, Gess & Ubell

[57] ABSTRACT

The object of this invention is to provide an extremely simple device to extract information to distinguish between obstructive apnea and central apnea and which performs this operation automatically based on the extracted information.

The device is equipped with analog signal processor 2 for generating pulse wave signals based on light received from a light emitting means and passing through or reflecting off living tissue; pulse wave base line analog signal processor 9 for extracting change components of a base line of the generated pulse wave signal; and master microcomputer 6 for distinguishing between obstructive apnea and central apnea on the basis of the extracted pulse wave base line change components.

11 Claims, 6 Drawing Sheets

RESPIRATION DIAGNOSIS APPARATUS

BACKGROUND OF THE INVENTION

1. Field of the Invention

The present invention relates to a respiration diagnosis apparatus which can either extract information to distinguish between obstructive apnea and central apnea or automatically perform such differentiation.

2. Description of the Prior Art

Conventionally, among respiration monitors, a monitor which detects the existence of respiration by detecting temperature differences between inspired air and expired air via a thermistor heat sensor inserted in the nasal cavity, a monitor which uses a microphone to detect the sound of breathing at the throat, a monitor which detects changes in the volume of the chest and/or abdomen during respiration via changes in electrical impedance, a monitor which detects changes in chest and/or abdominal measurements via a pressure sensor, distortion sensor, etc., and a monitor which detects via a pulse oximeter reduction in oxygen saturation in arterial blood accompanying apnea, as well as combinations of these monitors, have been proposed. In addition, it has already been announced that it is possible to estimate pleural pressure from respiratory changes in pulse waves.

There are two types of sleep apnea: sleep obstructive apnea, in which the thorax (abdomen) moves, but respiration does not occur due to an obstruction in the airway; and sleep central apnea, in which the thorax (abdomen) does not move. The basic maladies of these respiratory maladies differ, and the methods of their treatment differ as well. In conventional devices containing a heat sensor in the nasal cavity or a pulse oximeter, it was impossible to differentiate between these types of apnea. In addition, monitors which detected changes in chest (abdominal) volume, or in chest or abdominal measurements, could not detect sleep obstructive apnea. Therefore, a combination of several types of sensors was necessary to distinguish between central apnea and obstructive apnea. Moreover, attachment of pulse oximeters and respiratory sensors on patients was often required, which both patients and physicians found uncomfortable and inconvenient.

SUMMARY OF THE INVENTION

The object of this invention is to provide a respiration diagnosis apparatus which can, by means of an extremely simple device, either extract information to distinguish between obstructive apnea and central apnea or automatically perform such differentiation.

The respiration diagnosis apparatus of this invention, employing the fact that the base line of a pulse wave signal changes with respiration, as well as the fact that the nature of this change in the base line during obstructive apnea is different from that during normal respiration, either automatically differentiates between obstructive apnea and central apnea or extracts information (the amount of change in the base line) to allow performance of such differentiation. In addition, based on this pulse wave signal, the apparatus measures the level of arterial blood oxygen saturation, and based on this measurement differentiates between normal respiration and apnea.

When obstructive apnea is present, due to the movement of the thorax, internal thoracic pressure changes considerably during attempted respiration, which appears as a sharp change in the base line of the pulse wave signal. In other words, since the waveform of the changed pulse wave signal base line differs from that present during normal respiration, obstructive apnea may be distinguished from central apnea by detecting the change in the amplitude and/or waveform of the base line of the pulse wave signal.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

A detailed explanation of the embodiments of this invention is provided below with reference to the drawings.

Figure 1:
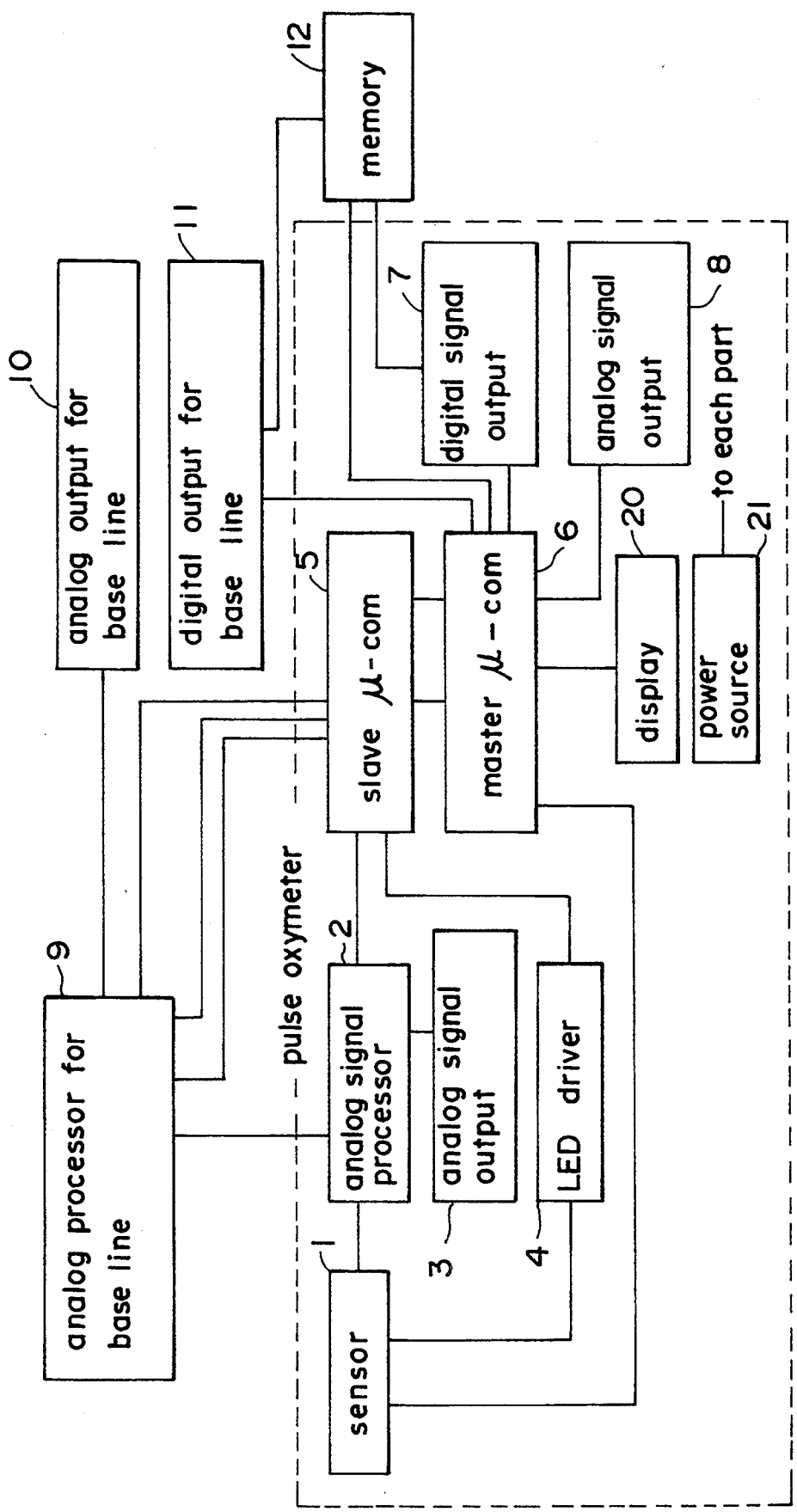
FIG. 1 is a block diagram showing the entire apparatus of one embodiment of the present invention.
Figure 2:
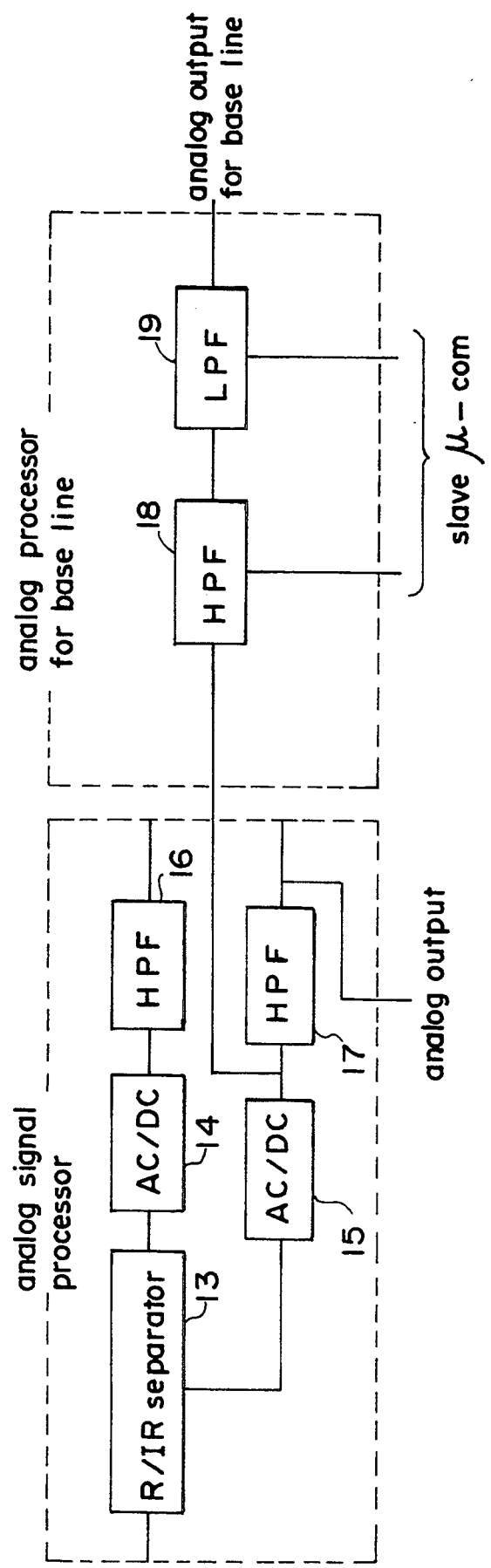
FIG. 2 is a block diagram showing the interiors of the analog signal processor and the pulse wave base line analog signal processor of FIG. 1.

FIG. 1 shows an embodiment of the present invention. Inside the dotted line is located a pulse oximeter unit, any of a number of publicly known designs of which may be used in the present invention. Sensor 1 is composed of an LED which emits red light (R-LED), an LED which emits near-infrared light (IR-LED), and a light receiving element, and is attached to the fingertip, etc. of the person being monitored. R-LED and IR-LED are driven by time-shared control signals from slave microcomputer 5 via LED drive circuit 4. Light which passes through or reflects off of the patient's fingertip, etc. is converted to an electrical signal via the light receiving element (not shown in the drawings), and is then input to analog signal processor 2. The light is separated into signal components of the light from R-LED and IR-LED by R/IR diverter 13 shown in FIG. 2 at analog signal processor 2. Each of these diverted signals is calculated in AC/DC unit 14 and AC/DC unit 15 according to a publicly-known method (AC component of each signal)/(DC component of each signal). The output from AC/DC unit 14 and AC/DC unit 15 undergoes A/D conversion at slave microcomputer 5 after passing through high-pass filter 16 and high-pass filter 17, through which AC/DC signals (pulse wave signals) pass with each heartbeat. Each signal undergoing A/D conversion at slave microcomputer 5 is input into master microcomputer 6 and shown on display unit 20, and the patient's arterial blood oxygen saturation level and pulse rate are calculated. The arterial blood oxygen saturation level and pulse rate calculated at master microcomputer 6 are output to external equipment via digital output unit 7 and analog output unit 8, are shown on display unit 20, and are stored along with the date and time in signal memory unit 12. In addition, the output from high-pass filter 17 is output as an analog pulse wave signal.

The above is part of a publicly-known oximeter, but it is acceptable if R-LED and IR-LED are not driven on a time-sharing basis, but are driven by a variable alternating frequency or variable alternating phase. A publicly-known circuit is used according to these methods in R/IR diverter 13. The output pulse wave signal from AC/DC unit 15 is input into pulse wave base line analog signal processor 9. Pulse wave base line analog signal processor 9 comprises high-pass filter 18 and low-pass filter 19 for passing the change components of the pulse wave signal base line accompanying respiration. In these filters, the cut-off frequencies are variable and the cut-off frequencies are set by slave microcomputer 5. The output from pulse wave base line analog signal processor 9 (base line signal) is output to external equipment via pulse wave base line analog output unit 10, as well as to master microcomputer 6 after undergoing A/D conversion at slave microcomputer 5. At microcomputer 6, the A/D converted base line signals are shown on display unit 20, and the signals' cycle (or, breaths per minute) and amplitude, as well as rise time and fall time, are calculated.

Figure 3A:
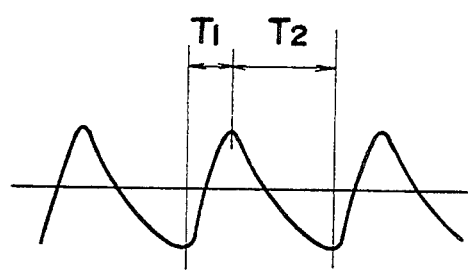
FIGS. 3(a) and 3(b) are a waveform chart of the base line of the pulse wave (base line signal) during normal conditions and during obstructive apnea.
Figure 3B:
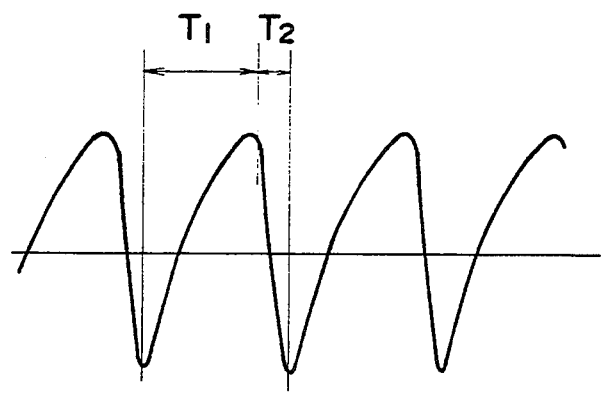

During normal respiration, the base line signals appear as shown in FIG. 3(a), whereas when sleep obstructive apnea is present, as shown in FIG. 3(b), the amplitude is larger and the waveform is different from normal, in that the ratios T1/T2, T1/(T1+T2) and T2/(T1+T2) for rise time T1 and fall time T2 differ from those present during normal respiration.

Figure 4:
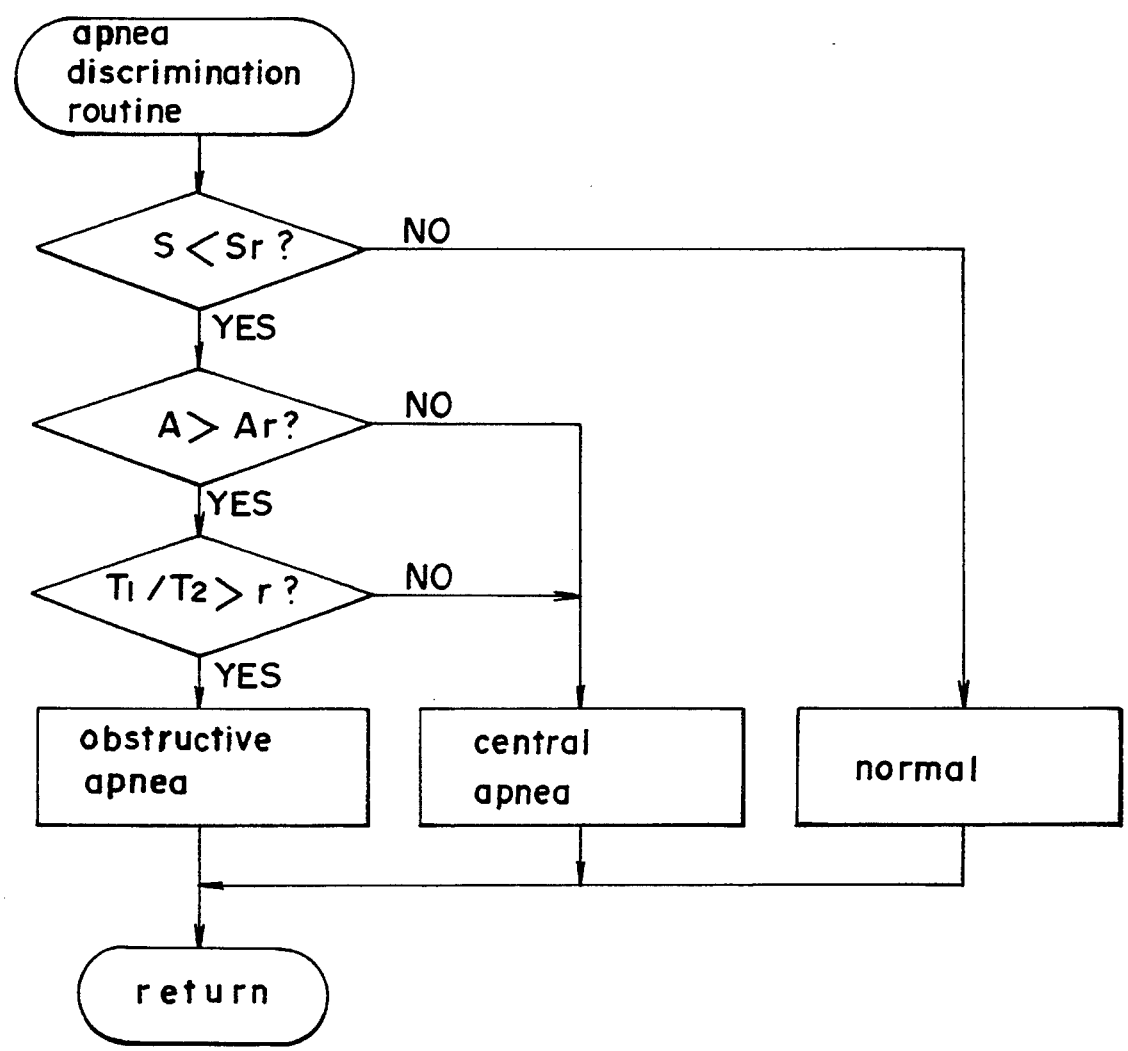
FIG. 4 is a flow chart of the process of differentiating between types of apnea.

The method employed by microcomputer 6 to identify obstructive apnea will now be explained using the flow chart in FIG. 4. First, arterial blood oxygen saturation value S measured by the pulse oximeter is compared to a corresponding standard value $S_r$ (which may be either a value set by the investigator or a fixed value), and if $S \geq S_r$, respiration is deemed normal. Where $S < S_r$, arterial blood oxygen saturation has fallen, which means that apnea is occurring, and the steps below are then followed to a determine if it is central apnea or obstructive apnea. First, base line signal amplitude A is compared to corresponding standard amplitude $A_r$ (which may be either a value set by the investigator or a fixed value), and if $A \leq A_r$, it is determined that central apnea is occurring. Where $A > A_r$, the rise time/fall time ratio (T1/T2) is compared with corresponding standard value r (which may be either a value set by the investigator or a fixed value). If $T1/T2 \leq r$, central apnea is determined to exist, whereas if $T1/T2 > r$, obstructive apnea is determined to exist. The use of both amplitude and the T1/T2 ratio provides increased accuracy, but the two types of apnea may be distinguished using either one individually. Master microcomputer 6 displays on display unit 20 either the cycle of the base line signal or the number of breaths per minute (hereinafter 'breaths'), as well as amplitude and T1/T2, and, in addition to outputting this information via pulse wave base line digital information output unit 11, stores it together with the date, time, arterial blood oxygen saturation level and pulse rate in signal memory unit 12 as described above.

In addition, where it is determined that obstructive apnea exists, a signal which indicates this to be the case (for example, the symbol 'H') is stored in signal memory unit 12. Where it is determined that central apnea exists, a different signal which indicates this to be the case (for example, the symbol 'C') is stored in signal memory unit 12. Further, the system may be made to emit an alarm based on sound or light when central or obstructive apnea is determined based on the amplitude of the base line signal, T1/T2 ratio and cycle (or the number of breaths per minute) and output by pulse wave base line digital output unit 11. Because the base line signal's amplitude and T1/T2 ratio increase during obstructive apnea, obstructive apnea may be detected even where the arterial blood oxygen saturation level is not known. One series of data stored in signal memory unit 12 comprises one file, and several files may be stored. Stored files may be displayed on display unit 20 by pushing a file output display button (not shown in the drawings) and output all at once from digital output unit 7 and/or analog output unit 8 in a short period of time. The memory medium for signal memory unit 12 may consist of a removable memory card, a magnetic memory medium, a read-write optical disk, etc., in which case the stored files may be removed from the device of this invention and read directly by a separate microcomputer.

Figure 5:
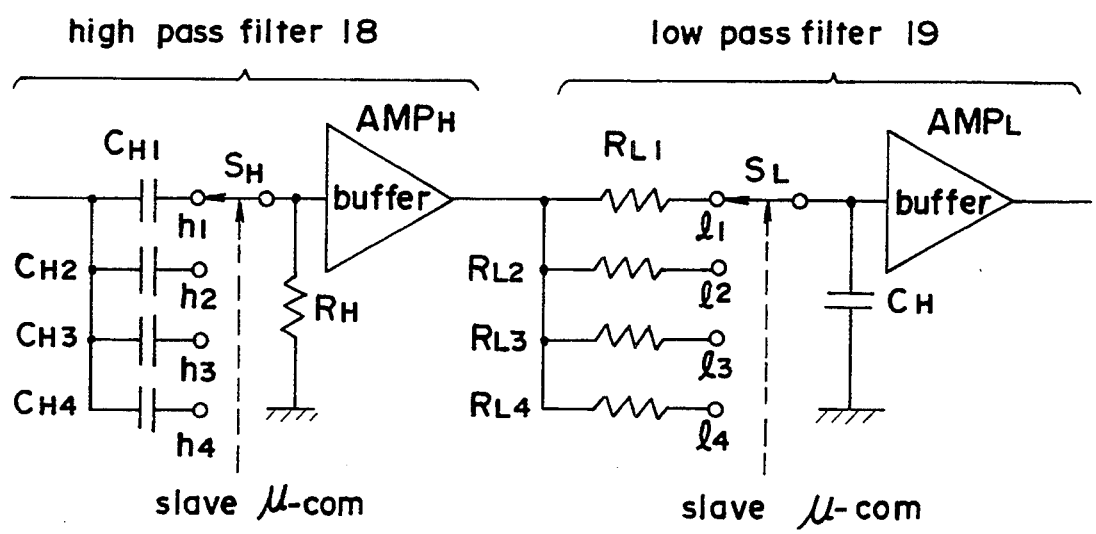
FIG. 5 is a specific construction diagram of the pulse wave base line analog signal processor.

Next, the setting of the cut-off frequency for the pulse wave base line analog signal processor is explained. FIG. 5 shows one embodiment of pulse wave base line analog signal processor 9. The cut-off frequencies of high-pass filter 18 are alternated by alternating among condensers CH1 to CH4 via switch SH. Similarly, the cut-off frequencies of low-pass filter 19 are alternated by alternating among resistors RL1 to RL4 via switch SL. The cut-off frequencies among which high-pass filter 18 may be alternated are 0.125 Hz (position h1), 0.25 Hz (h2), 0.5 Hz (h3), and 1 Hz (h4), while those for low-path filter 19 are 0.5 Hz (position l1), 1 Hz (l2), 2 Hz (l3), and 4 Hz (l4). When the power switch is turned on, switch SH is in position hi and a cut-off frequency of 0.125 Hz (hereinafter fHO) is selected, while switch SL is in position i1 and a cutoff frequency of 4 Hz (hereinafter fLO) is selected. When the pulse rate is measured by the pulse oximeter unit, the position for switch SL corresponding to that rate is selected. In other words, the position of switch SL is selected so that fLO is the smallest value satisfying the condition $fP \leq fLO$, where the pulse wave signal frequency calculated (by master microcomputer 6) from the measured pulse rate is fP, and the signal to set this is output from master microcomputer 6 via slave microcomputer 5. Initially, where fHO is selected, the cycle, etc. of the base line signal is calculated by master microcomputer 6 in the manner described above. When the cycle of the base line signal has been calculated, the frequency of the base line signal fPB is calculated by master microcomputer 6. Then the position of switch SH is selected so that the value of fHO is the largest satisfying the equation $fPB \geq fHO$, and the signal to set this is output from master microcomputer 6 via slave microcomputer 5.

Figure 6:
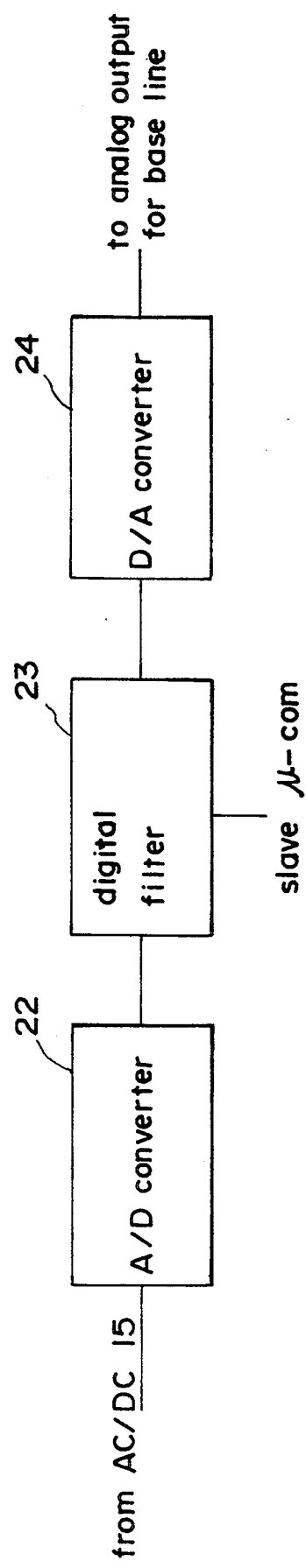
FIG. 6 is a block diagram of a pulse wave base line analog signal processor employing a digital filter.

In the embodiment shown in FIG. 5, four cut-off frequencies may be selected for high-pass filter 18 and low-pass filter 19, but a larger number may be selected, and cut-off frequencies may be continuously set using a publicly-known method. In addition, one filter is being used in FIG. 5, but the use of several filters is more effective in eliminating pulse wave signal components. Furthermore, both a high-pass filter and a low-pass filter are used in FIG. 5, but a single band-pass filter may also be used. Moreover, FIG. 5 uses a filter employing an analog circuit, but it may also be constructed as in FIG. 6, using a digital filter 23 which carries out filtering via digital calculation using a publicly known method, after A/D conversion of the output from AC/DC unit 15 using A/D converter 22. In this case, an extremely precise filter in which the setting of cut-off frequencies is simple may be obtained, and elimination of pulse wave signal components may be effectively carried out.

In this embodiment, a photoelectric pulse wave signal obtained from the pulse oximeter's sensor is used to measure the breaths based on the cycle of base line change component: instead, however, breaths may also be measured from the cycle of change components of the base line of a plethysmogram signal via publicly known impedance plethysmograpy, etc., or by a publicly-known pressure pulse wave employing a pressure sensor or stress sensor, and moreover the type of apnea may be distinguished from the amplitude and waveform using a method similar to that of the above embodiment.

In the respiration diagnosis appratus of this invention, by extracting changes in the base line of a pulse wave signal, central apnea and obstructive apnea may be easily distinguished. Furthermore, the level of arterial blood oxygen saturation may be measured by means of a pulse wave signal. Based on the measured arterial blood oxygen saturation level, apnea may be distinguished from normal respiration.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A respiration diagnosis apparatus, comprising:
    a means for emitting light;
    a means for receiving the light emitted from the light emitting means and passing through or reflected by living tissue, and for detecting a pulse wave based on the received light;
    a means for generating a pulse wave signal in accordance with the detected pulse wave; and
    a means for extracting a change component of the base line of the generated pulse wave signal.

2. A respiration diagnosis apparatus as claimed in claim 1, further comprising:
    a means for distinguishing between obstructive apnea and central apnea based on the extracted change component.

3. A respiration diagnosis apparatus as claimed in claim 2, further comprising:
    a means for calculating the amplitude of the extracted change component,
    wherein the distinguishing means carries out its operation on the basis of the calculated amplitude.

4. A respiration diagnosis apparatus as claimed in claim 2, further comprising:
    a means for calculating a value with reference to the ratio of rise time to fall time of the extracted change component,
    wherein the distinguishing means carries out its operation on the basis of the calculated value.

5. A respiration diagnosis apparatus as claimed in claim 2, further comprising:
    a first means for calculating the amplitude of the extracted change component; and
    a second means for calculating a value with reference to the ratio of rise time to fall time of the extracted change component,
    wherein the distinguishing means carries out its operation on the basis of the calculated amplitude and the calculated value.

6. A respiration diagnosis apparatus as claimed in claim 2, further comprising:
    a means for measuring oxygen saturation in arterial blood on the basis of the detected pulse wave,
    wherein the distinguishing means further distinguishes between a normal condition and an apnea condition.

7. A respiration diagnosis apparatus, comprising;
    a means for emitting light;
    a means for receiving the light emitted from the light emitting means and passing through or reflected by living tissue, and for detecting a pulse wave based on the received light;
    a means for generating a pulse wave signal in accordance with the detected pulse wave; and
    a means for distinguishing between obstructive apnea and central apnea on the basis of the generated pulse wave signal.

8. A respiration diagnosis apparatus for determining apnea comprising:
    means for receiving a signal representative of a patient's heartbeat, pulse wave, and blood oxygen saturation;
    first means for determining the blood oxygen saturation from the signal and comparing it with a predetermined value to determine if an apnea is occurring;
    second means for determining, when the first means has determined apnea; a base line signal amplitude of the pulse wave from the signal and comparing it with a predetermined value to determine if an obstructive apnea has occurred; and
    means for indicating an obstructive apnea condition.

9. A respiration diagnosis apparatus as claimed in claim 8 further including a third means for determining a rise time period $T_1$, and a fall time period $T_2$ of the base line of the pulse wave and comparing these time periods with a predetermined value to also determine if an obstructive apnea has occurred.

10. A respiration diagnosis apparatus, comprising:
    means for emitting light;
    means for receiving the light emitted from the light emitting means and passing through or reflected by living tissue, and for generating a pulse wave signal;
    means for extracting a change component of the base line of the generated pulse wave signal;
    means for calculating a value with reference to a ratio of a rise time to a fall time of the change component; and
    means for distinguishing between obstructive apnea and central apnea based on the change component.

11. A respiration diagnosis apparatus, comprising:
    means for emitting light;
    means for receiving the light emitted from the light emitting means and passing through or reflected by living tissue, and for generating a pulse wave signal;
    means for extracting a change component of the base line of the generated pulse wave signal;

first means for calculating the amplitude of the change component;

second means for calculating a value with reference to a ratio of a rise time to a fall time of the change component; and means for distinguishing between obstructive apnea and central apnea based on the calculated amplitude and the calculated value.

* * * * *